(12) United States Patent
Mo

(10) Patent No.: US 11,627,928 B2
(45) Date of Patent: Apr. 18, 2023

(54) 3D BONE DENSITY AND BONE AGE CALCULATION APPARATUS USING ARTIFICIAL INTELLIGENCE-BASED ROTATION MANNER

(71) Applicant: WEVER INSTRUMENTS CO., LTD, Uijeongbu-si (KR)

(72) Inventor: Seong Hui Mo, Seoul (KR)

(73) Assignee: WEVER INSTRUMENTS CO., LTD, Uijeongbu-si (KR)

( * ) Notice: Subject to any disclaimer, the term of this patent is extended or adjusted under 35 U.S.C. 154(b) by 39 days.

(21) Appl. No.: 17/142,451

(22) Filed: Jan. 6, 2021

(65) Prior Publication Data

US 2021/0204895 A1  Jul. 8, 2021

(30) Foreign Application Priority Data

Jan. 8, 2020  (KR) ........................ 10-2020-0002613

(51) Int. Cl.
*A61B 6/00* (2006.01)
*A61B 6/03* (2006.01)
*A61B 6/04* (2006.01)

(52) U.S. Cl.
CPC .............. *A61B 6/505* (2013.01); *A61B 6/035* (2013.01); *A61B 6/0407* (2013.01);
(Continued)

(58) Field of Classification Search
CPC ........... A61B 6/032; A61B 6/035; A61B 6/04; A61B 6/0407; A61B 6/0478; A61B 6/0487; A61B 6/42; A61B 6/4208; A61B 6/4225; A61B 6/4233; A61B 6/4241; A61B 6/44; A61B 6/4429; A61B 6/4435; A61B 6/46; A61B 6/461; A61B 6/465; A61B 6/466; A61B 6/467; A61B 6/469; A61B 6/482;
(Continued)

(56) References Cited

U.S. PATENT DOCUMENTS

| | | | | |
|---|---|---|---|---|
| 4,124,799 A | * | 11/1978 | Schittenhelm | A61B 6/4035 378/18 |
| 4,829,549 A | * | 5/1989 | Vogel | A61B 6/505 378/146 |
| 5,432,834 A | * | 7/1995 | Gershman | A61B 6/505 378/146 |
| 5,748,704 A | * | 5/1998 | Mazess | A61B 6/482 378/54 |

(Continued)

FOREIGN PATENT DOCUMENTS

| KR | 102045223 | 11/2019 |
|---|---|---|
| KR | 20190142234 | 12/2019 |

*Primary Examiner* — Allen C. Ho
(74) *Attorney, Agent, or Firm* — Cantor Colburn LLP

(57) ABSTRACT

Provided is a 3D bone density and bone age calculation apparatus using an artificial intelligence-based rotation manner. The 3D bone density and bone age calculation apparatus includes a main body, and the main body includes a rotary drum including a drum shaft gear, an X-ray generator, an intensifying screen, and an image data capturer, a drum driver including a motor shaft gear connected to the drum shaft gear so as to rotate the rotary drum, a motor, support rollers and one of an origin sensor and an encoder, an outer case and an inner case, a front case and a rear case, a capturing holder, and a controller configured to select an image-captured position of the rotary drum, and configured to input a current age, sex and nutritional status of a patient, (Continued)

etc. The controller includes a display configured to display captured images and a diagram indicating bone age.

2 Claims, 6 Drawing Sheets

(52) U.S. Cl.
CPC .......... *A61B 6/0478* (2013.01); *A61B 6/4225* (2013.01); *A61B 6/4435* (2013.01); *A61B 6/466* (2013.01); *A61B 6/467* (2013.01); *A61B 6/5205* (2013.01); *A61B 6/5294* (2013.01); *A61B 6/544* (2013.01); *A61B 2503/04* (2013.01); *A61B 2503/08* (2013.01)

(58) Field of Classification Search
CPC ......... A61B 6/505; A61B 6/52; A61B 6/5205; A61B 6/5294; A61B 6/54; A61B 6/542; A61B 6/544; A61B 6/545
USPC .......... 378/19, 54, 62, 98.8, 98.9, 196–198, 378/38–40, 189, 192; 250/370.09
See application file for complete search history.

(56) References Cited

U.S. PATENT DOCUMENTS

| | | | | |
|---|---|---|---|---|
| 6,007,243 A * | 12/1999 | Ergun | ................... | H04N 5/357 |
| | | | | 378/197 |
| 6,215,846 B1 * | 4/2001 | Mazess | ................ | A61B 6/548 |
| | | | | 348/E5.088 |
| 6,490,339 B2 * | 12/2002 | Mitchell | .............. | A61B 6/4216 |
| | | | | 378/62 |
| 6,676,291 B2 * | 1/2004 | Ahn | ...................... | A61B 6/505 |
| | | | | 378/68 |
| 8,348,506 B2 * | 1/2013 | Yorkston | ............. | A61B 6/4452 |
| | | | | 378/4 |
| 9,044,186 B2 * | 6/2015 | Ma | ....................... | A61B 6/4042 |
| 9,116,248 B2 * | 8/2015 | Abenaim | ................ | G01T 1/243 |
| 9,119,590 B2 * | 9/2015 | Budoff | ................. | A61B 6/5205 |
| 9,125,611 B2 * | 9/2015 | Eaves | .................. | A61B 6/4441 |
| 9,198,630 B2 * | 12/2015 | Grant | .................... | A61B 6/032 |
| 9,274,037 B2 * | 3/2016 | Huwer | ................. | G01N 23/046 |
| 9,717,467 B2 * | 8/2017 | Litzenberger | .......... | A61B 6/025 |
| 10,945,697 B2 * | 3/2021 | Goto | ................... | A61B 6/5211 |

* cited by examiner

3D BONE DENSITY AND BONE AGE CALCULATION APPARATUS USING ARTIFICIAL INTELLIGENCE-BASED ROTATION MANNER

BACKGROUND OF THE INVENTION

Field of the Invention

The present invention relates to a 3D bone density and bone age calculation apparatus using an artificial intelligence-based rotation manner, and more particularly to a 3D bone density and bone age calculation apparatus using an artificial intelligence-based rotation manner which may acquire the best bone images by capturing an image of a body region of a patient, such as a hand or a foot, at a desired position and continuously capturing images of the body region, and provide an artificial intelligence data unit configured to provide data regarding the bone age, the chronological age and the predicted height of the patient using artificial intelligence within a short time.

Description of the Related Art

X-ray examination, ultrasonography, etc. are used as bone density measurement methods and, in the case of X-ray examination, several X-ray images of a patient are captured in an X-ray lab, which is conventionally used in orthopedic offices, an orthopedic surgeon must inspect multiple X-ray images individually, and thus a wide margin of error may be introduced.

Further, in this case, the time for which the patient is exposed to radiation is lengthened, thus adversely affecting a human body. Meanwhile, in the case of ultrasonography, it may be very difficult to acquire and read a bone density image by acquiring a picture of structures within the human body using ultrasound.

In addition, it is very difficult to set a reference value using an apparatus for diagnosing growth plates and data, and the facilities investment costs for forming equipment are high. Further, a conventional bone density measurement apparatus is difficult to use to measure the bone densities of wrists and heels and also difficult to adjust the position of a device for emitting X-rays. Therefore, in order to solve these conventional problems, the present invention suggests a diagnosis apparatus for calculating bone density and bone age which includes a detachable ankle holder so as to easily measure the density of the bones of the heel, i.e., calcaneus, and the wrist.

However, because the above diagnosis apparatus for calculating bone density and bone age performs image capturing at a fixed position but a patient frequently moves the back of his/her hand or changes the position of his/her ankle, a doctor, the patient, an examiner, etc. are greatly inconvenienced.

Further, through the diagnosis apparatus, it is difficult to precisely analyze data, such as bone age, etc., and numerical errors in the data occur depending on the image-captured position of the human body and thus cause errors in determination of bone age, and it takes a long time to analyze the data.

RELATED ART DOCUMENT

Patent Document (Patent Document 1) Korean Patent Unexamined Publication No. 1020190142234 (Dec. 26, 2019)

(Patent Document 2) Korean Patent Registration No. 102045223 (Nov. 11, 2019)

SUMMARY OF THE INVENTION

Therefore, the present invention has been made in view of the above problems, and it is an object of the present invention to provide a 3D bone density and growth plate diagnosis apparatus using artificial intelligence which includes a separate case so as to easily replace an intensifying screen and to acquire precise images.

It is another object of the present invention to provide a 3D bone density and growth plate diagnosis apparatus using artificial intelligence which may capture an image of a human body at a desired position while measuring bone density and opening or closing of growth plates in 3D.

It is a further object of the present invention to provide a 3D bone density and bone age calculation apparatus which implements an artificial intelligence-based rotation manner so that a user or a patient may conveniently use the apparatus.

In accordance with the present invention, the above and other objects can be accomplished by the provision of a 3D bone density and bone age calculation apparatus using an artificial intelligence-based rotation manner, including a main body, wherein the main body includes a rotary drum including a drum shaft gear formed on an outer circumferential surface thereof, an X-ray generator configured to radiate X-rays, an intensifying screen mounted at a position facing the X-ray generator, and an image data capturer configured to directly acquire images from a front surface of the intensifying screen, a drum driver including a motor shaft gear formed on an outer surface thereof and connected to the drum shaft gear so as to rotate the rotary drum, a motor, support rollers formed on a lower surface of the rotary drum so as to support the rotary drum, and one of an origin sensor and an encoder provided on the rotary drum so as to capture images at a desired position, an outer case and an inner case provided to surround the rotary drum, a front case having insertion rail grooves formed thereon and a rear case having insertion rail grooves formed thereon, respectively provided at front and rear ends of the inner and outer cases, a capturing holder provided within the inner case so as to be fixed during X-ray image capturing, and a controller configured to select an image-captured position of the rotary drum so as to perform continuous image capturing and intensive image capturing of a body part, selected from a hand, a foot and other body parts of a patient, from a desired angle or from multiple angles, and configured to input a current age, sex and nutritional status of a patient, whether or not the patient begins menstruation if the patient is a female, etc. The controller includes a display configured to display captured images and a diagram indicating bone age.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
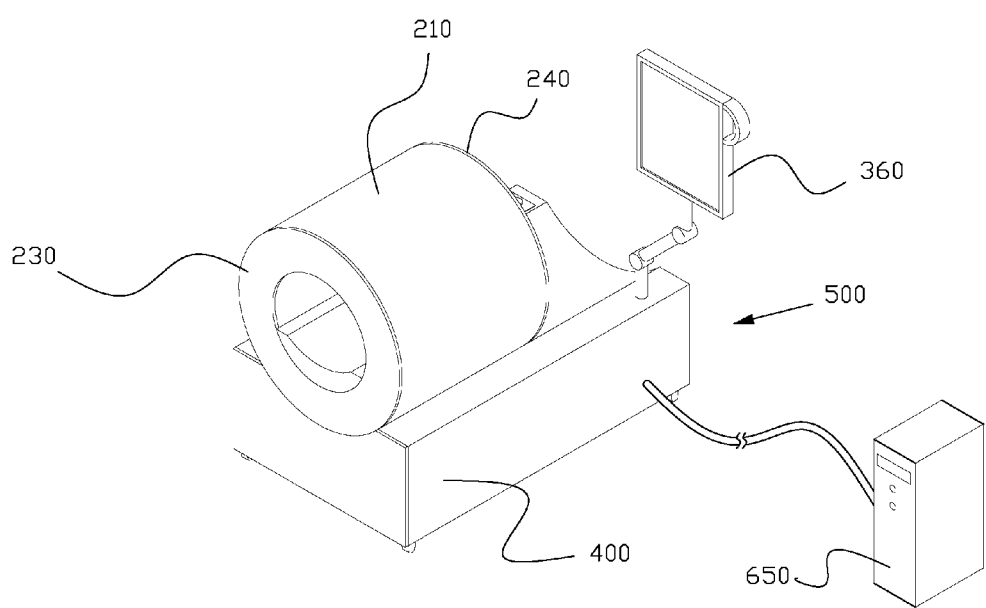
FIG. 1 is a perspective view of a 3D bone density and bone age calculation apparatus using an artificial intelligence-based rotation manner according to one exemplary embodiment of the present invention.
Figure 2:
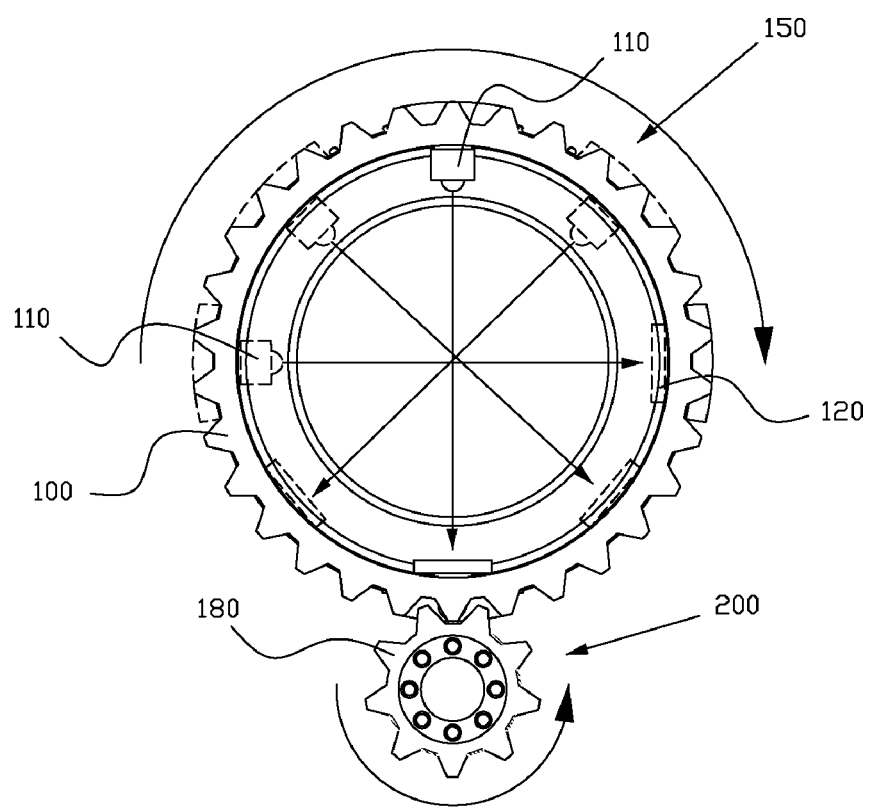
FIG. 2 is a view illustrating the operating states of a drum and a driver according to the present invention.
Figure 3:
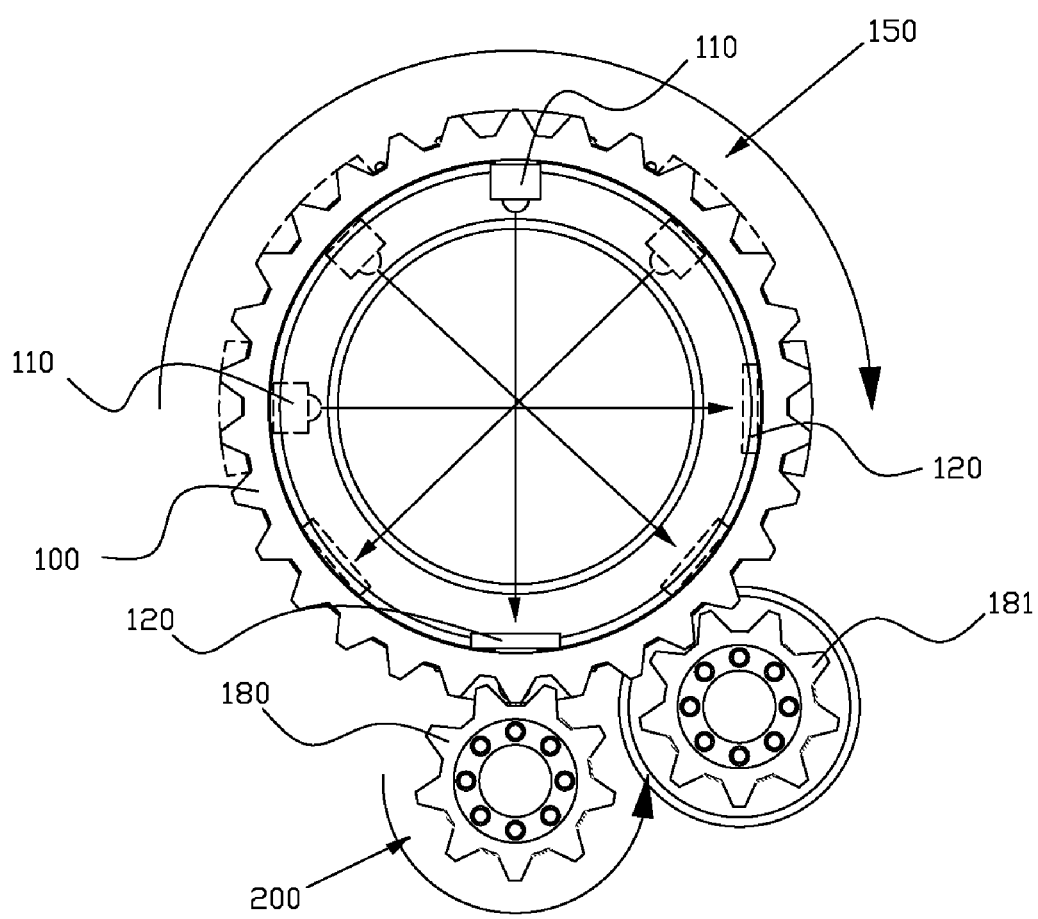
FIG. 3 is an exploded perspective view of a 3D bone density and bone age calculation apparatus using an artificial intelligence-based rotation manner according to the present invention.
Figure 4:
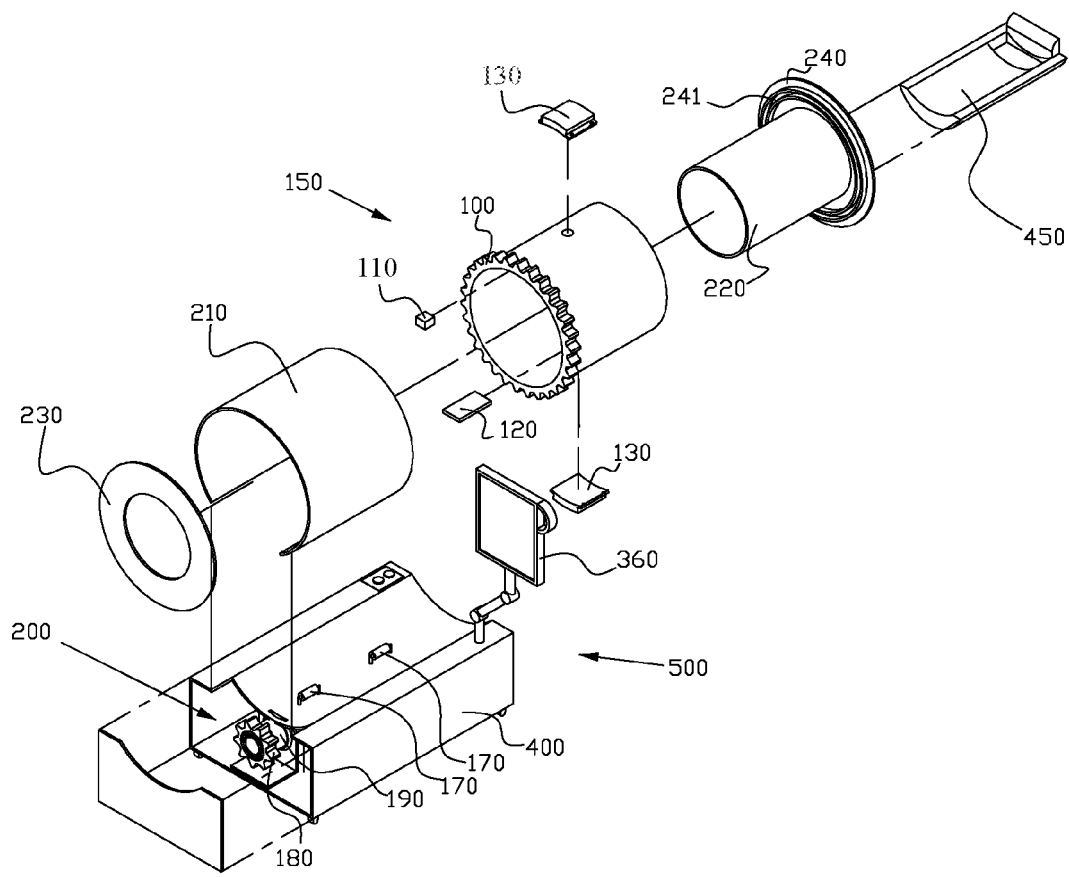
FIG. 4 is a view illustrating the operating state of the 3D bone density and bone age calculation apparatus according to the present invention.
Figure 5:
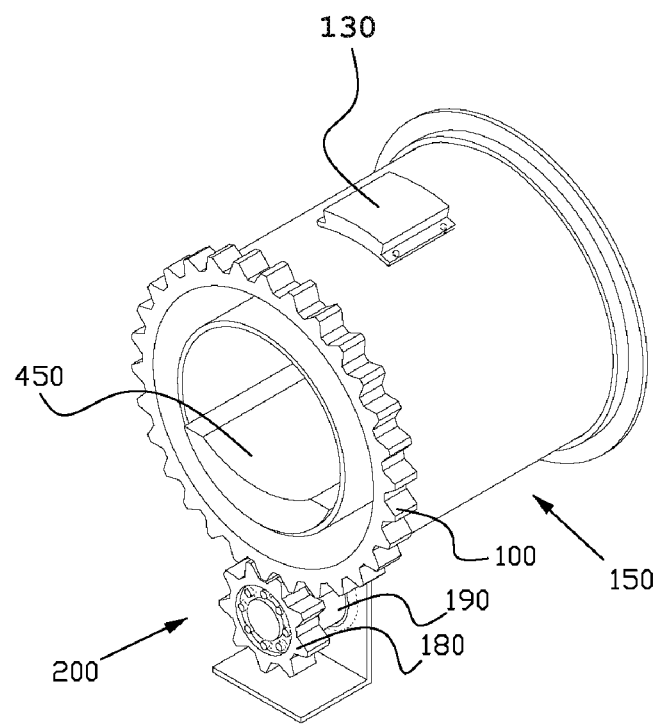
FIG. 5 is a view illustrating the operating state of a driver of a 3D bone density and bone age calculation apparatus using an artificial intelligence-based rotation manner according to another embodiment of the present invention.
Figure 6:
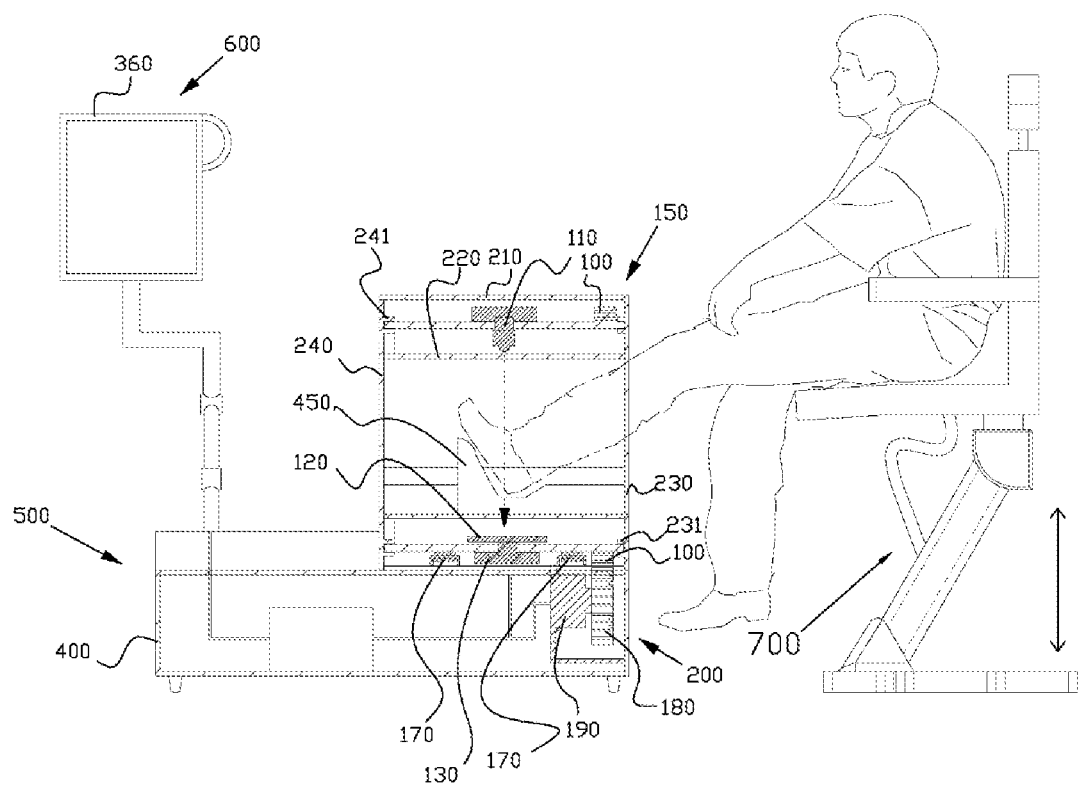
FIG. 6 is a view illustrating the usage state of the 3D bone density and bone age calculation apparatus according to the present invention.

Reference will now be made in detail to various embodiments of the present invention, examples of which are illustrated in the accompanying drawings and described below. While the invention will be described in conjunction with exemplary embodiments, it will be understood that the present description is not intended to limit the invention to the exemplary embodiments. On the contrary, the invention is intended to cover not only the exemplary embodiments, but also various alternatives, modifications, equivalents and other embodiments, which may be included within the spirit and scope of the invention as defined by the appended claims. Wherever possible, the same reference numbers will be used throughout the drawings to refer to the same or like parts. Further, in the following description of the embodiments, terms, such as "first" and "second", are used only to describe various elements, and these elements should not be construed to be limited by these terms. These terms are used only to distinguish one element from other elements. For example, a first element described hereinafter may be termed a second element, and similarly, a second element described hereinafter may be termed a first element, without departing from the scope of the invention. As used herein, the term "and/or" includes any and all combinations of one or more of the associated listed items. When an element or layer is referred to as being "connected to" or "coupled to" another element or layer, it may be directly connected to or coupled to the other element or layer, or intervening elements or layers may be present. In contrast, when an element is referred to as being "directly connected to" or "directly coupled to" another element or layer, there may be no intervening elements or layers present.

The terminology used herein is for the purpose of describing particular exemplary embodiments only and is not intended to be limiting. In the following description of the embodiments, singular expressions may encompass plural expressions, unless they have clearly different contextual meanings. In the following description of the embodiments, terms, such as "comprising", "including", "having", etc., will be interpreted as indicating the presence of characteristics, numbers, steps, operations, elements or parts stated in the description or combinations thereof, and do not exclude the presence of one or more other characteristics, numbers, steps, operations, elements, parts or combinations thereof, or the possibility of adding the same.

Hereinafter, reference will now be made in detail to the preferred embodiments of the present invention, examples of which are illustrated in the accompanying drawings. Wherever possible, the same reference numbers will be used throughout the drawings to refer to the same or like parts.

A 3D bone density and bone age calculation apparatus using an artificial intelligence-based rotation manner according to the present invention has the following configuration.

The 3D bone density and bone age calculation apparatus according to the present invention includes a main body 500, and the main body 500 includes a rotary drum 150 including a drum shaft gear 100 formed on the outer circumferential surface thereof, an X-ray generator 110 configured to radiate X-rays, an intensifying screen 120 mounted at a position facing the X-ray generator 110, and an image data capturer 130 configured to directly acquire images from the front surface of the intensifying screen 120, a drum driver 200 including a motor shaft gear 180 formed on the outer surface thereof and connected to the drum shaft gear 100 so as to rotate the rotary drum 150, a motor 190 and support rollers 170 formed on the lower surface of the drum driver 200 so as to support the rotary drum 150, an outer case 210 and an inner case 220 provided to surround the rotary drum 150, and a controller 600 configured to select the image-captured position of the rotary drum 150 so as to perform continuous image capturing and intensive image capturing of a body part, selected from a hand, a foot, and other body parts of a patient, from a desired angle or from multiple angles, and configured to input the current age, sex and nutritional status of the patient, whether or not the patient begins menstruation if the patient is a female, etc. The controller 600 includes a display 360 configured to display captured images and a diagram indicating bone age. The controller 600 may further include an artificial intelligence data unit 650 configured to provide data about the bone age, the chronological age and the predicted height of the patient by comparing captured images of the desired body part, such as a finger or a foot, to data of an age group within the minimum range learned using data which is pre-input to artificial intelligence.

The main body 500 is characterized in that the inner and outer cases 220 and 210 are provided, the rotary drum 150 is formed so as to be rotated within the inner and outer cases 220 and 210, the support rollers 170 configured to support the rotary drum 150 are formed thereunder, and a lower case 400 is configured to accommodate the motor shaft gear 180 and the motor 190 therein.

A front case 230 provided with insertion rail grooves 231 formed thereon and a rear case 240 provided with insertion rail grooves 241 formed thereon are respectively provided at the front and rear ends of the inner and outer cases 220 and 210.

The rotary drum 150 includes the drum shaft gear 100 formed on the outer circumferential surface thereof, the X-ray generator 110 configured to radiate X-rays, the intensifying screen 120 mounted at the position facing the X-ray generator 110, and the image data capturer 130 configured to directly acquire images from the front surface of the intensifying screen 120, and is configured so as to be rotatable by about 300 degrees.

The rotary drum 150 is configured such that, when a desired angle is input, the motor 190 is rotated and then, when the motor 190 is stopped, image capturing is performed, or image capturing is performed at the positions of respective position sensors (not shown) provided at an interval of 10 degrees. 18 position sensors are located at an interval of 10 degrees from 0 degree to 180 degrees, and a camera is located at a desired position so as to capture an X-ray image. In the present invention, the rotary drum 150 may be configured so as to be rotatable by about 300 degrees. However, 360-degree rotation of the rotary drum 150 falls within the scope of the invention.

The support rollers 170 configured to support the rotary drum 150 are formed at front and rear portions of the lower end of the rotary drum 150, thereby supporting the weight of the rotary drum 150 and enabling the rotary drum 150 to be smoothly rotated.

The drum driver 200 is configured such that the motor shaft gear 180 is engaged with the drum shaft gear 100 formed on the outer circumferential surface of the rotary drum 150, and the motor shaft gear 180 is connected to the motor 190 so as to be driven.

A capturing holder 450 is provided at the upper portion of the inner case 220 so as to be fixed during X-ray image capturing, thereby enabling convenient X-raying of the patient.

The rotary drum 150 of the main body 500 includes the X-ray generator 110 configured to radiate X-rays, the intensifying screen 120 mounted at the position facing the X-ray generator 110, and the image data capturer 130 configured to directly acquire images from the front surface of the intensifying screen 120 and then to produce image data are provided. Thereby, the 3D bone density and bone age calculation apparatus according to the present invention radiates X-rays to bones or tissues adjacent thereto, and may thus acquire images, calculate bone density, diagnose whether or not growth plates are opened, and measure a wrist and an ankle.

The image data capturer 130 transmits the image data to the display 360, and simultaneously, the artificial intelligence data unit 650 provides data about the bone age, the chronological age and the predicted height of the patient through an artificial intelligence determiner.

The artificial intelligence data unit 650 selects one of its own data stored therein and external data for providing charged information, compares measured data to a corresponding one of the selected data through the artificial intelligence determiner, and provides the result of comparison to a doctor or an examiner.

Further, the main body 500 or a height-adjustable chair 700 is configured such that the height thereof may be automatically adjusted for infants, the elderly and the weak, and thus, the height of the main body 500 or the height-adjustable chair 700 may be conveniently adjusted during X-ray image capturing.

The drum driver 200 according to the present invention is configured such that the motor 190 is driven and thus rotates the rotary drum 150 to a desired position, which is input, using an origin sensor or an encoder 181 provided on the rotary drum 150, and the rotary drum 150 is controlled to be rotated and then stopped at the desired position, which is input through the controller 600. When the controller 600 sets a measurement position, the motor 190 is driven to move the motor shaft gear 180 by a corresponding angle so that the rotary drum 150 is rotated only to the rotation position due to the encoder 181. Here, the angle is set to about 300 degrees so that the rotary drum 150 may be rotated at the angle from the regular position thereof, i.e., the center thereof, and then X-ray image capturing may be performed at the set measurement position and continuous X-ray image capturing may be performed.

As such, X-ray image capturing may be performed from multiple angles, thereby being capable of making accurate diagnosis and enabling the patient to be conveniently X-rayed without moving to change the angle of his/her body part during X-ray image capturing.

As is apparent from the above description, the present invention provides a 3D bone density and bone age calculation apparatus using an artificial intelligence-based rotation manner which may capture images of a desired position of the body part of a patient so as to precisely measure the body part, and particularly, may enable precise and rapid analysis of data using artificial intelligence and perform 3D image capturing so as to be conveniently used for X-ray image capturing.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A 3D bone density and bone age calculation apparatus using an artificial intelligence-based rotation manner, comprising:
  a main body,
  wherein the main body comprises:
    a rotary drum comprising a drum shaft gear formed on an outer circumferential surface thereof, an X-ray generator configured to radiate X-rays, an intensifying screen mounted at a position facing the X-ray generator, and an image data capturer configured to directly capture images from a front surface of the intensifying screen;
    a drum driver comprising a motor shaft gear formed on an outer surface thereof and connected to the drum shaft gear so as to rotate the rotary drum, a motor, support rollers formed on a lower surface of the rotary drum so as to support the rotary drum, and one of an origin sensor and an encoder provided on the rotary drum so as to capture images at a desired position;
    an outer case and an inner case provided to surround the rotary drum;
    a front case having insertion rail grooves formed thereon and a rear case having insertion rail grooves formed thereon, respectively provided at a front end and a rear end of the inner case and the outer case;
    a capturing holder provided within the inner case so as to be fixed during X-ray image capturing; and
    a controller configured to select an image-captured position of the rotary drum so as to perform continuous image capturing and intensive image capturing of a body part, selected from a hand, a foot, and other body parts of a patient, from a desired angle or from multiple angles, and configured to input a current age, sex, and nutritional status of a patient, whether or not the patient begins menstruation if the patient is a female, the controller including a display configured to display the captured images and a diagram indicating a bone age,
    wherein the controller comprises an artificial intelligence data unit configured to provide data about the bone age, a chronological age, and a predicted height of the patient by comparing the captured images of the body part to data of an age group within a minimum range learned using data, which is pre-input to artificial intelligence, and
    wherein the image data capturer transmits the captured images to the display, and simultaneously, the artificial intelligence data unit provides the data about the bone age, the chronological age, and the predicted height of the patient through an artificial intelligence determiner.

2. The 3D bone density and bone age calculation apparatus according to claim 1, further comprising: a height-adjustable chair,
   wherein one of the main body and the height-adjustable chair is configured such that a height thereof is automatically adjustable for infants, the elderly, and the weak, and thus, the height thereof is conveniently adjustable during X-ray image capturing.

\* \* \* \* \*